United States Patent [19]

Turcotte et al.

[11] Patent Number: 4,910,342
[45] Date of Patent: Mar. 20, 1990

[54] POLYALKYLENE POLYAMINES VIA VAPOR PHASE REACTION

[75] Inventors: Michael G. Turcotte, Allentown; Cawas A. Cooper, Macungie, both of Pa.

[73] Assignee: Air Products and Chemicals, Inc., Allentown, Pa.

[21] Appl. No.: 49,648

[22] Filed: May 12, 1987

[51] Int. Cl.$^4$ ........................................... C07C 85/06
[52] U.S. Cl. ................................................ 564/479
[58] Field of Search .................................... 564/479

[56] References Cited

U.S. PATENT DOCUMENTS

| | | | |
|---|---|---|---|
| 3,121,115 | 2/1964 | Mealy | 260/570.5 |
| 4,036,881 | 7/1977 | Brennan | 260/583 P |
| 4,314,083 | 2/1982 | Ford | 564/479 |
| 4,362,886 | 12/1982 | Ford | 564/479 |
| 4,394,524 | 7/1983 | Ford | 564/479 |
| 4,399,308 | 8/1983 | Ford | 564/479 |
| 4,609,761 | 9/1986 | Watts et al. | 564/479 |
| 4,617,418 | 10/1986 | Ford et al. | 564/479 |
| 4,720,588 | 1/1988 | Turcotte et al. | 564/479 |

FOREIGN PATENT DOCUMENTS 0093434 11/1983 European Pat. Off. ............. 564/479
0093983 11/1983 European Pat. Off. ............. 564/479

Primary Examiner—Werren B. Lone
Attorney, Agent, or Firm—Russell L. Brewer; James C. Simmons; William F. Marsh

[57] ABSTRACT

This invention pertains to an improved process for preparing noncyclic polyalkylene polyamine compounds in high selectivity by reacting an alkanolamine and an alkylene amine in the presence of an acidic catalyst. The improvement resides in effecting the reaction under fixed bed catalytic conditions and maintaining the reaction conditions such that a vapor phase condition exists for the reaction mixture comprising both reactants and products. To accomplish the formation of vapor phase conditions, sufficient alkylenediamine is injected into the feedstream along with alkanolamine, temperature is maintained from 200°–280° C., and pressure ranges from about 0 psig to 150 psig so that the dew point temperature of the reaction product mix is below the reaction temperature at reaction pressure.

8 Claims, 2 Drawing Sheets

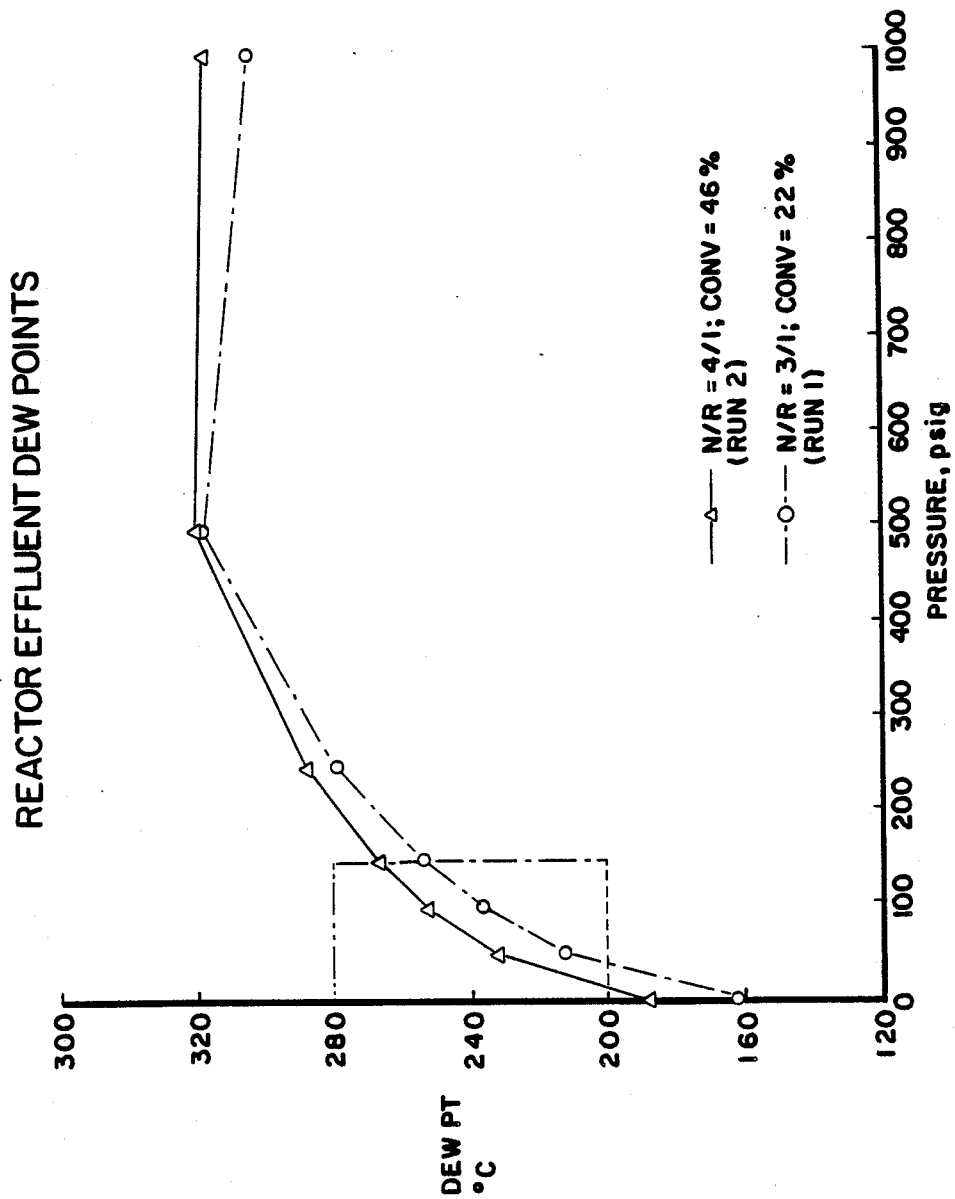

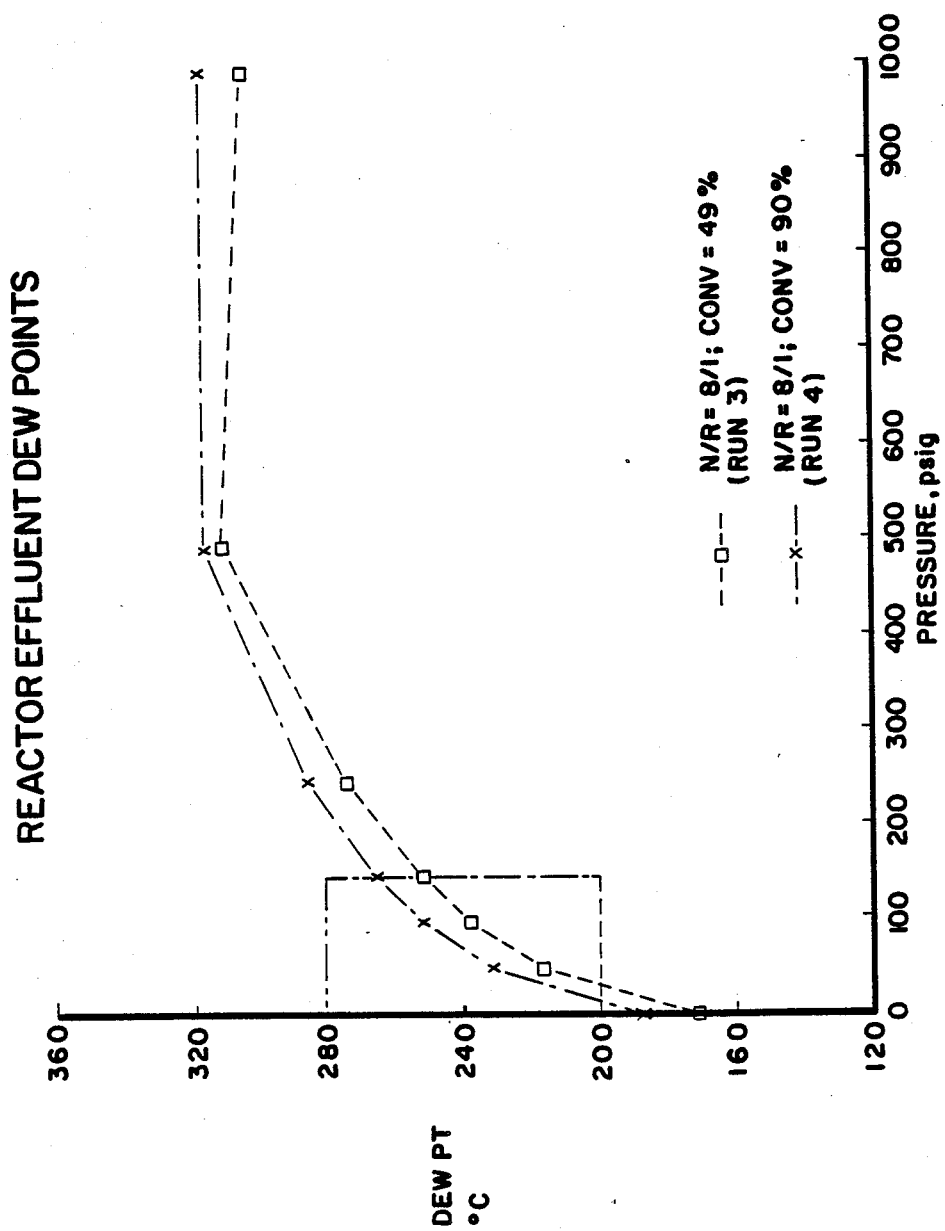

POLYALKYLENE POLYAMINES VIA VAPOR PHASE REACTION

TECHNICAL FIELD

This invention relates to the preparation of polyalkylene polyamines from an alkylene amine and alkanolamine under vapor phase conditions.

BACKGROUND OF THE INVENTION

The condensation of a hydroxy-containing compound with an amine to liberate water is well known. In many instances, the condensation has been effected by using an acid catalyst, such as a phosphorus-containing compound. The ability to effect intermolecular condensation of a hydroxy-containing compound with an amine has been of substantial interest in the preparation of polyalkylene polyamines, particularly polyethylene polyamines.

A variety of polyalkylene polyamines can be formed by the basic reaction of the hydroxy compound and amine compound. However, one of the objectives in the preparation of polyalkylene polyamines has been to maximize the intermolecular condensation to form the linear or noncyclic polyalkylene polyamine as opposed to effecting an intramolecular condensation of such compounds which convert to the cyclic amine. The former amines are utilized in preparing lubricant formulations, acid gas scrubbing compositions, and the like. Numerous patents have issued since the 1960's which illustrate various embodiments for preparing linear polyalkylene polyamines in high selectivity by reacting an alkylene amine and an alkanolamine in the presence of an acidic catalyst. Representative patents include:

U.S. Pat. No. 3,121,115, discloses the reaction of an amine with an alkanolamine in the presence of a phosphorus-containing compound to produce alkylated amines. Reaction conditions used were 200°–350° C. and pressures ranged from atmospheric to super atmospheric.

U.S. Pat. No. 4,036,881 discloses the preparation of polyalkylene polyamines, particularly polyethylene polyamines, by the reaction of monoethanolamine and ethylenediamine under liquid phase conditions. An acidic phosphorus-containing compound was utilized to effect catalysis of the reaction. Representative catalyst systems included alkyl and aryl phosphinic acids, phosphoric and phosphorous acid compounds and their anhydrides, and metal phosphates such as iron, aluminum and boron phosphate and so forth. The patentees pointed out that it was important to maintain liquid phase conditions in the reaction zone for achieving high selectivity to linear polyethylene polyamines. If vapor phase conditions were encountered, as shown in Example 12, then selectivity to linear polyethylene polyamines was sacrificed.

Other patents which show the preparation of polyethylene polyamines or broadly, polyalkylene polyamines under liquid phase conditions include U.S. Pat. Nos. 4,394,524; 4,399,308; 4,362,886; 4,314,083; and European patent applications Nos. 0,093,434 and 0,093,983.

The above patents described various processes for producing polyalkylene polyamines using a variety of acidic catalytic systems such as, for example, Lewis acids, arsenic, antimony or bismuth salts; a variety of phosphorus containing catalyst systems including phosphoric acid, boron phosphate, as noted in the Brennan, et al., U.S. Pat. No. 4,036,881 patent, and phosphoramides. Each process involves the reaction of an alkanolamine with an alkylene amine compound at temperatures from about 175°–300° C., and preferably temperatures in excess of 225° C. to produce linear polyalkylene polyamines. Each process employs conditions which maintain the reactants in liquid phase, and thus the reaction pressure is controlled to the extent necessary to maintain such liquid phase conditions at reaction temperature.

U.S. Pat. No. 4,394,524 differs slightly from the processes described above in that ammonia is included as an additional reactant to convert alkanolamine to an alkylene amine in situ. With the utilization of ammonia, higher selectivities to polyethylene polyamines were reported. However, pressures were maintained such that the reaction was carried out in essentially liquid phase.

Although the above liquid phase processes result in producing linear polyalkylene polyamines in relatively high selectivity, the processes suffer from a series of processing disadvantages. The processing disadvantages arise because of the solubility of the catalyst systems in the reactants or reaction products. This is particularly true in the case of phosphorus-containing catalytic compounds in that high proportions of phosphorous are recovered in the reaction product and must be removed. This is typically done by distillation. An additional problem associated with these processes is that the catalyst must be continually replaced or replenished.

SUMMARY OF THE INVENTION

This invention relates to an improvement in a process for producing noncyclic polyalkylene polyamines in high selectivity. The basic process comprises:

contacting (a) an alkylene amine compound having two primary amino groups with the general formula:

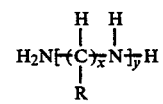

wherein

R is hydrogen or a lower alkyl ($C_1$–$C_4$) radical;

x is a number from 2 to about 6; and y is a number from 1 to about 4; with (b) an alkanolamine compound having primary or secondary hydroxyl groups of the general formula:

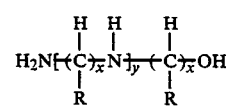

wherein

R is hydrogen or a lower alkyl ($C_1$–$C_4$) radical;

x is a number from 2 to about 6; and y is a number from 0 to about 3.

This contacting is carried out in the presence of an effective amount of an acidic catalyst system, and at a temperature sufficient to effect reaction between the alkylene amine compound and alkanolamine compound. The improvement in the basic process and constituting the invention comprises:

passing the reactants into a catalytic reactor packed with a solid phase acidic catalyst;

effecting the reaction under conditions such that the reactor contents remain essentially in the vapor phase, said reaction being carried out within a temperature range from about 200°-280° C., and within a pressure range from about 0 psig to 150 psig and an alkylene amine compound to alkanolamine mole ratio of 2 to 12:1. Vapor phase conditions are maintained within the temperature and pressure range by controlling temperature, pressure and conversion such that the dew point temperature of the reactor contents in the reaction zone is reduced to a level lower than said reaction temperature.

There are numerous advantages associated with the practice of this invention. One of the advantages is that there is no need for catalyst separation from the reaction product in view of the low concentration of catalyst material therein. Another is that the process readily lends itself to continuous operation. A third advantage is that the reaction is carried out at relatively low pressures, at least lower than those required for many liquid phase conditions thus providing for energy savings. A fourth is that one can achieve very high selectivity to linear polyalkylene polyamines. A fifth is that the process can be carried out using the same catalyst for extended periods of time. A sixth is that ammonia or inert gas may be eliminated, the presence of which adds to separation problems.

DRAWINGS

FIGS. 1-2 are dew point temperature diagrams wherein dew point temperature is plotted at various molar reactant ratios of ethylene diamine (E) to monoethanolamine (R) and conversions for a range of pressures.

DETAILED DESCRIPTION OF THE INVENTION

The invention relates to a process for synthesizing noncyclic polyalkylene polyamines and preferably linear and branched polyethylene polyamines, such as diethylene triamine and high homologues. In the process, an alkylene amine having two primary amino groups and, preferably, an unbranched alkylene moiety, such as ethylene diamine is reacted with an alkanolamine having a primary or a secondary hydroxy moiety and a primary amino group. The alkylene amine reactants which typically can be used in practicing the process are represented by the general formula:

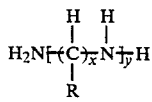

wherein

R is a hydrogen or a lower alkyl; ($C_1$–$C_4$) radical;
x is a number from 2 to about 6; and
y is a number from 1 to about 4.

A preferred R radical is hydrogen, while the x value is 2 and the y value is 1. Examples of alkyleneamine compounds suited for the reaction include 1,3-propylene diamine, 1,2-propylene diamine, diethylene triamine, triethylene tetramine and ethylene diamine. The latter diamine is the preferred alkylene amine compound for preparing linear polyethylene polyamines.

The alkanolamine reactants which can be used in the process and represented by the formula:

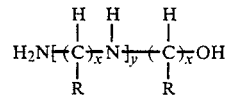

wherein

R is hydrogen or a lower alkyl ($C_1$–$C_4$) radical;
x is a number from 2 to about 6, and y is a number from 0 to 3.

A preferred R radical is hydrogen while x is 2 and y is 0. Examples of alkanolamine compounds suited for practicing the process are monoethanolamine, isomeric propanolamines, and N-(2)-aminoethyl(ethanolamine). Monoethanolamine is preferred.

Linear and branched polyalkylene polyamines that are produced by the reaction of an alkylene amine and an alkanolamine as described above, are represented by the general formula:

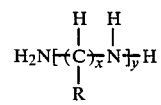

wherein

R is a hydrogen or a lower alkyl ($C_1$–$C_4$) radical, preferably a methyl radical;
x is a number from 2 to about 6;
y is a number from 2 to about 6 and
x may vary for a given value of y.

Examples of linear polyalkylene polyamines that are produced in accordance with the process of this invention include dipropylene triamine, tributylene tetramine and various polyethylene polyamines such as diethylene triamine, triethylene tetramine and tetraethylene pentamine. Other types of polyamines include di(2-methylethylene) triamine, tri(2-methylethylene) tetramine and N-(2-aminoethyl)1,3-propylene diamine.

A variety of acidic catalytic systems can be utilized for effecting condensation of the hydroxyl group of the alkanolamine with the alkylene amine compound and numerous catalytic systems have already been described in the Background Portion of this Application and such catalysts are incorporated by reference; i.e., from U.S. 4,036,881; European 0 093 434 and U.S. 4,394,524. In view of the fact that the reaction is carried out under vapor phase conditions, the catalyst is material capable of being compounded as a particulate material or capable of being supported by a solid phase carrier. The nonvolatile catalytic systems may be incorporated upon or impregnated into an inert support. Silica, carbon and zeolites are representative of the latter. By utilizing a catalyst system, which is in solid phase form, a fixed bed catalytic reactor can be utilized to effect the condensation of the alkanolamine and alkylene amine reactant system under continuous conditions.

Catalyst systems suited for effecting intermolecular condensation include the phosphorus containing compounds such as boron phosphate, aluminum phosphate, phosphorous and phosphoric acid on silica or carbon, ammonium hydrogen phosphate e.g. mono and diammonium hydrogen phosphate, strontium and rare earth metal acid phosphates such as lanthanum acid phosphates, yttrium acid phosphates, gadolinium acid phosphates, thorium acid phosphates, neodymium acid phosphates, praseodymium acid phosphates, samarium acid phosphates or mixtures of lanthanum acid phosphate with other rare earth metal acid phosphates. The rare earth metals suited are scandium, yttrium, lanthanum, and those in the lanthanide series of the periodic table having an atomic number from 59-71 and the rare earth actinides having atomic numbers 89 to 92. Such phosphorus-containing catalysts are shown in U.S. Pat. Nos. 4,036,881 and 4,463,193 and are incorporated by reference. Rare earth and hydrogen exchanged zeolites can be used provided the cage structure is sufficiently large; e.g., greater than about 8A° to permit formation of the amine. Other catalytic systems include halide salts such as zinc chloride, the sulfur and nitrogen containing acids and salts such as nitric acid, sulfuric acid, berylium sulfate, ammonium nitrate, etc. These catalysts can be used so long as they are effective as solid phase catalysts under the conditions specified in the reaction zone for effecting condensation. Antimony, bismuth and arsenic salts can also be used. Experience has shown phosphoric acid and ammonium hydrogen phosphate on a support, e.g., silica are extremely effective catalysts.

The basic difference between this process and the processes described and utilized heretofore in the preparation of polyalkylene polyamines resides in the selective control of temperature between 200°-280° C., and preferably 245° to about 270° C., pressure from 0 psig to about 150 psig, preferably 30-75 psig, and a mole ratio of alkyleneamine to alkanolamine of 2 to 12:1, and preferably of 3 to 9:1. Parameters are controlled by the adjustment of these variables such that the mixture of reactants and reaction products are maintained in the vapor phase. For example, at low temperatures, e.g., 200°-220° C., higher mole ratios of alkyleneamine to alkanolamine may be required, otherwise liquid phase conditions might be encountered. If liquid phase conditions are encountered in the reaction zone, then the concentration of catalyst in the reaction product leaving the reactor, if soluble, may increase substantially, and catalyst must be replaced in the reactor. In addition the catalyst may agglomerate and plug the reactor.

In order to achieve high selectivity to linear or branched polyalkylene polyamines under vapor phase conditions the reaction temperature must be above the dew point temperature of the reactor contents but at a temperature less than 280° C. Although the condensation reaction can be effected at temperatures above 280° C. as indicated in the prior art, selectivity to linear polyalkylene polyamines decreases substantially as the temperature is increased above that level when using vapor phase conditions. The lowest temperature suited for practicing this invention is that temperature at which the catalyst is catalytically effective for generating polyalkylene polyamines via the intermolecular condensation of the alkanolamine and alkylene amine.

The condensation reaction is carried out at pressure sufficient to effect the reaction of alkanolamine with the alkylene amine. More particularly under the present process, the pressure will range from about 0 psig to 150 psig, and preferably from about 30 to 75 psig. Higher pressures serve no useful purpose and may require the addition of ammonia or inert gas to maintain vapor phase conditions which leads to an additional separation problem.

The generation of vapor phase conditions in the process, with concomitant high selectivity to linear polyalkylene polyamines is unique. In the prior art, as exemplified by Brennan, et al. in the U.S. Pat. No. 4,036,881 patent, selectivity to linear polyalkylene polyamines was sacrificed when vapor phase conditions were employed in the reaction of monoethanolamine and ethylene diamine. Although not intending to be bound by theory, it is belived there are two primary reasons for high selectivity to cyclics in the Brennan et al example. First the reaction was carried out at too high of a process temperature and second the process pressure (atmospheric) was too low for the mole ratio (1:1) of alkyleneamine to alkanolamine used. On the other hand in accordance with the invention described here, the temperature of the components of the reaction zone is below a preselected reaction temperature, e.g., 280° C., at reaction pressure (max. 150 psig). By increasing the amount of alkyleneamine in the reaction zone, e.g., to a mole ratio of 2:1 and higher and reducing pressure, one can then lower the dew point temperature of the contents in the reaction zone and thereby establish a condition in which vapor phase conditions exist throughout the process. The selection of pressure, temperature and mole ratio of reactants then permits one to achieve high selectivity typically achieved previously only under liquid phase conditions.

Dew point temperatures can be derived from vapor-liquid equilibria for feed and products at various conditions. These vapor-liquid equilibria can be calculated using standard chemical engineering techniques. For example the following articles can be reviewed for producing computer or mathematical models for calculating specific temperature conditions. These articles are:

1. Zellner, et al., Industrial Engineering Chemical Fundamentals,
Vo. 9, Nov. 9, 549–564 (1970);

2. Abrams, et al., AICHE Journal, Vol. 21, No. 116–128 (1975). Both of these articles are incorporated by reference.

To alleviate some of the necessity for calculations, FIGS. 1-2 have been provided showing correlations between dew point temperature and conversion for specific ethylenediamine/monoethanolamine feed ratio as a function of reaction pressure. The systems shown relate to production of polyethylene polyamines from ethylene diamine (E), and monoethanolamine (R). In these systems, the indicated mole ratios of ethylenediamine and monoethanolamine have been reacted to provide the indicated conversions to total polyethylene polyamines (Table I, Runs 1-4). The dew point of each crude product mixture (which consists of unreacted ethylenediamine and monoethanolamine, and higher polyethylene polyamine products) was then calculated as a function of pressure, and the results plotted in FIGS. 1 and 2. If other mole ratios of ethylenediamine and monoethanolamine, or if other reactants are employed, these correlations would not apply and additional calculations of dew point temperature against pressure would have to be made. It also follows that additional calculations would have to be made if conversion levels were significantly different than the levels shown in the drawings.

If one prefers not to calculate reactor conditions necessary for vapor phase conditions, one can use physical characteristics of the process to make that determination. The latter technique, though may require some experimentation. One of the easiest methods for determining whether liquid or mixed phase conditions exist in the reactor is to monitor reactor product composition. For example if a phosphorus catalyst is used, high levels, e.g., greater than 20 ppm catalyst levels, in the reaction product indicate the presence of some liquid phase. This is because of the solubility of the catalyst in the reactant and products. An increasing pressure drop or modification of catalyst structure, e.g. rounded corners of pellets, etc. will also reveal this feature if some liquid phase is present. If such conditions exist the reaction temperature must be increased unless such temperature exceeds 280° C. In the latter instance, the pressure must be decreased.

The following examples are provided to illustrate various embodiments of the invention as well as to illustrate some of the differences between the process described herein and other processes utilized in the prior art.

EXAMPLE 1

A series of reactions was carried out under various operating conditions. In those instances where vapor phase conditions were utilized or attempted, the reaction was carried out in a stainless steel packed bed reactor filled with solid phase catalyst pellets consisting of phosphoric acid on silica or diammonium hydrogen phosphate on silica. The feeds were introduced into the top of the reactor and the reactants passed downflow over the catalyst bed. The reaction product was withdrawn from the bottom of the reactor as a vapor. The pressure was maintained in the reactor by a backpressure regulator and gauge pressure measured.

Runs indicated as being carried under liquid phase conditions were carried out in a stirred autoclave as in the prior art. Conditions are given.

Table 1 provides a description of the reaction conditions for producing polyethylene polyamines and such conditions include the usage of various catalysts, reaction temperatures, pressures, liquid hourly space velocity (LHSV), mole ratio of ethylenediamine to monoethanolamine, reaction times (where appropriate) and comments with respect to whether liquid phase conditions existed during the reaction, and if high catalyst concentrations were present in the reaction product.

TABLE I

LOW PRESSURE POLYAMINE PRODUCTION

| Run | Temp (°C.) | Pressure (psig) | Catalyst | GHSV$^a$ (hr$^{-1}$) | LHSV$^b$ | EDA | MELA | NH$_3$ | Phosphate Content (ppm) | Comments |
|---|---|---|---|---|---|---|---|---|---|---|
| 1 | 248 | 43 | 1* | 1484 | | 3 | 1 | | | Gas Phase$^c$ |
| 2 | 252 | 43 | 1 | 711 | | 4 | 1 | | | Gas Phase$^c$ |
| 3 | 259 | 43 | 1 | 695 | | 8 | 1 | | | Gas Phase$^c$ |
| 4 | 280 | 64 | 1 | 706 | | 8 | 1 | | | Gas Phase$^c$ |
| 5 | 240 | 44 | 2* | 1481 | | 5.3 | 1 | | <1 | Gas Phase |
| 6 | 240 | 47 | 2 | 893 | | 8.2 | 1 | | <1 | Gas Phase |
| 7 | 260 | 50 | 2 | 353 | | 5.2 | 1 | | <1 | Gas Phase |
| 8 | 249 | 61 | 2 | 341 | | 8.2 | 1 | | <1 | Gas Phase |
| 9 | 251 | 6 | 2 | 725 | | 1 | 1 | | | Gas Phase |
| 10 | 304 | 8 | 2 | 719 | | 1 | 1 | | | Gas Phase |
| 11 | 249 | 3 | 2 | 686 | | 1.95 | 1 | | | Gas Phase$^c$ |
| 12 | 300 | 5 | 2 | 671 | | 1.95 | 1 | | | Gas Phase$^c$ |
| 13 | 251 | 5 | 2 | 749 | | 2.99 | 1 | | | Gas Phase$^c$ |
| 14 | 299 | 10 | 2 | 761 | | 2.99 | 1 | | | Gas Phase$^c$ |
| 15 | 265 | 1400 | | | 1.5 | 1 | 1 | 6.9 | 32.2 | Liquid Phase; U.S. Pat. No. 4,617,418 |
| 16 | 250 | 250 | | | 3 | 2 | 1 | 4 | 14.25 | Mixed Phases; U.S. Pat. No. 4,617,418 |
| 17 | 250–400 | 0.7 | | | 1.56–3.35$^d$ | | 1 | 1 | | Vapor phase, prior art U.S. Pat. No. 4,036,881 Continuous tubular reactor |

| Comparative Run | Temp (°C.) | Pressure (psig) | Catalyst | GHSV$^a$ (hr$^{-1}$) | EDA | MELA | Phosphate Content (ppm) | Comments |
|---|---|---|---|---|---|---|---|---|
| 1-C | 299 | 47 | 2* | 667 | 3 | 1 | | Gas Phase |
| 2-C | 301 | 50 | 2 | 761 | 1 | 1 | | Gas Phase |
| 3-C | 324 | 51 | 2 | 671 | 3 | 1 | | Gas Phase |
| 4-C | 322 | 61 | 2 | 754 | 1 | 1 | | Gas Phase |
| 5-C | 252 | 54 | 2 | 676 | 1 | 1 | 35 | Liquid Phase |
| 6-C | 231 | 51 | 2 | 679 | 1 | 1 | 111 | Liquid Phase |
| 7-C | 221 | 56 | 2 | 715 | 1 | 1 | 371 | Liquid Phase |

*1 H$_3$PO$_4$/SiO$_2$
*2 (NH$_4$)$_2$HPO$_4$/SiO$_2$
$^a$Gas hourly space velocity, based on EDA and MELA.
$^b$Liquid hourly space velocity, based on EDA and MELA.
$^c$Determined by comparison with FIGS. 1 and 2.
$^d$Based on EDA, MELA, and nitrogen. Mole ratio of nitrogen to equimolar EDA/MELA feed not specified.
*2 (NH$_4$)$_2$HPO$_4$/SiO$_2$

TABLE II

PRODUCT DISTRIBUTION$^a$

| | PIP$^b$ | AEP$^c$ | DETA$^d$ | AEEA$^e$ | TETA(NC)$^f$ | TETA(C)$^g$ | TEPA(NC)$^h$ | TEPA(C)$^i$ | UNK$^j$ | Sel NC$^k$ | Conv$^l$ (%) |
|---|---|---|---|---|---|---|---|---|---|---|---|
| Run | | | | | | | | | | | |
| 1 | 2.7 | 0.8 | 72.6 | 15.2 | 7.5 | 0 | 0 | 0 | 1.2 | 81.1 | 22.3 |
| 2 | 2.4 | 3.5 | 54.0 | 1.4 | 17.5 | 3.2 | 11.7 | 3.0 | 3.3 | 82.2 | 46.3 |
| 3 | 1.7 | 2.0 | 67.4 | 0.4 | 16.1 | 1.9 | 8.6 | 1.2 | 0.7 | 92.1 | 48.7 |

TABLE II-continued
PRODUCT DISTRIBUTION[a]

|  | PIP[b] | AEP[c] | DETA[d] | AEEA[e] | TETA(NC)[f] | TETA(C)[g] | TEPA(NC)[h] | TEPA(C)[i] | UNK[j] | Sel NC[k] | Conv[l] (%) |
|---|---|---|---|---|---|---|---|---|---|---|---|
| 4 | 2.7 | 5.0 | 60.5 | 0 | 13.5 | 4.3 | 5.4 | 3.1 | 5.5 | 79.4 | 90.3 |
| 5 | 2.5 | 2.8 | 65.8 | 4.9 | 14.5 | 1.8 | 2.2 | 0.7 | 4.9 | 82.5 | 23.1 |
| 6 | 1.6 | 1.4 | 74.9 | 1.0 | 12.3 | 1.0 | 0.6 | 0.3 | 6.8 | 87.8 | 33.9 |
| 7 | 1.9 | 4.0 | 56.8 | 0 | 15.1 | 4.9 | 4.6 | 3.1 | 9.6 | 76.5 | 84.1 |
| 8 | 1.6 | 1.9 | 66.3 | 0 | 12.3 | 2.2 | 3.6 | 1.4 | 10.6 | 82.2 | 72.3 |
| 9 | 5.1 | 11.6 | 25.6 | 4.6 | 9.2 | 14.2 | 3.5 | 10.7 | 15.5 | 38.3 | 27.3 |
| 10 | 10.8 | 13.8 | 7.8 | 0.1 | 2.4 | 8.0 | 0.1 | 2.4 | 54.6 | 10.3 | 97.5 |
| 11 | 3.7 | 8.2 | 37.5 | 3.0 | 12.0 | 10.3 | 4.7 | 7.5 | 13.1 | 54.2 | 27.8 |
| 12 | 10.9 | 13.4 | 13.3 | 0.2 | 2.1 | 6.2 | 0.4 | 2.3 | 50.2 | 15.8 | 87.6 |
| 13 | 3.1 | 6.5 | 45.8 | 2.0 | 13.0 | 9.0 | 4.3 | 6.9 | 9.4 | 63.1 | 28.1 |
| 14 | 10.3 | 13.1 | 14.4 | 0 | 2.5 | 8.5 | 0.5 | 3.9 | 46.8 | 17.4 | 93.0 |
| 15 | 3.06 | 4.32 | 50.38 |  | 17.00 | 1.34 | 15.07 |  |  | 83 | 43 |
| 16 | 3.52 | 4.71 | 45.99 |  | 14.80 | 3.56 | 12.37 |  |  | 72 | 33 |
| 17 | m | m | m | m | m | m |  |  |  |  |  |
| Comparative Run |  |  |  |  |  |  |  |  |  |  |  |
| 1-C | 11.4 | 13.2 | 24.8 | 0 | 3.8 | 7.6 | 0.5 | 2.9 | 35.8 | 29.1 | 82.0 |
| 2-C | 11.3 | 6.7 | 6.9 | 0.5 | 4.2 | 8.6 | 0.8 | 3.0 | 58.0 | 11.9 | 83.3 |
| 3-C | 14.3 | 12.4 | 15.0 | 0 | 2.0 | 5.6 | 0.2 | 1.8 | 48.7 | 17.2 | 99.2 |
| 4-C | 13.5 | 7.1 | 2.6 | 0.3 | 0.6 | 2.3 | 0.1 | 0.3 | 73.2 | 3.3 | 98.5 |
| 5-C | 6.1 | 10.3 | 32.6 | 5.5 | 13.5 | 8.0 | 7.2 | 4.9 | 11.9 | 53.3 | 40.0 |
| 6-C | 5.7 | 9.0 | 28.4 | 22.4 | 5.9 | 5.4 | 5.0 | 2.7 | 15.5 | 39.3 | 19.0 |
| 7-C | 5.3 | 6.4 | 25.3 | 38.6 | 5.7 | 3.5 | 2.2 | 1.4 | 11.6 | 33.2 | 7.7[n] |

[a]Feedstock-free, water-free, weight-normalized basis
[b]Piperazine
[c]N-(2-aminoethyl)piperazine
[d]Diethylenetriamine
[e]Aminoethylethanolamine
[f]Triethylenetetramine, linear and branched isomers
[g]Triethylenetetramine, cyclic isomers
[h]Tetraethylenepentamine, linear and branched isomers
[i]Tetraethylenepentamine, cyclic isomers
[j]Reaction by-products
[k]Selectivity to noncyclic polyamines
[l]Conversion of MELA
[m]Not specified by U.S. Pat. No. 4,036,881; products are described as "complex and highly cyclic".
[n]Continued operation under these conditions rapidly (<3 days) led to conversions of <1.0%, owing to removal of phosphoric acid from the catalyst bed.

Table II provides the results in terms of the quantities of various components in the reaction product in weight percent. The analysis was done by the use of gas chromatography.

Runs 1-8 were carried out at low pressure and temperatures ranging from approximately 245° to 290° C. The mole ratio were varied from 3 to 8:1 EDA to MELA. Conversion for these runs ranged from a low of about 22% at the lowest EDA to MELA mole ratio to a high of 90% at a temperature of 280° C. Selectively to noncyclics was greater than 75% in all cases with significant conversion to DETA.

Runs 9-14 provide results at essentially atmospheric pressure, and again show the beneficial effect of operation with a molar excess of alkylenediamine, and particularly ethylenediamine, in the reactor feed at reaction temperatures below 280° C. Although the reaction is a gas phase reaction, poor selectivity to noncyclic polyethylene amines is obtained with 1/1, 2/1, and 3/1 molar ethylenediamine/monoethanolamine feed ratios above 280° C. (Runs 10, 12, and 14). However, at temperatures below 280° C., e.g., about 250° C., predominantly noncyclic polyamines are obtained with 2/1 and 3/1, but not 1/1, molar ethylenediamine/monoethanolamine (EDA/MEA) feed ratios (Runs 11, 13, and 9, respectively). Conversions with the 2/1 and 3/1 feeds are within the range of those obtained in the preferred operating range (Runs 1-8). Thus, predominantly noncyclic polyethylene amines can be produced by vapor phase reaction of monoethanolamine in the presence of a molar excess of ethylenediamine at essentially atmospheric pressure, although somewhat higher selectivities to noncyclic products are obtained within the preferred operating pressure range.

Comparative runs 1-C to 4-C show that as reaction temperature is increased above 280° C. at mole ratios suited for the invention selectivity drops off dramatically (Runs 1-C and 3-C). At lower mole ratios, e.g., 1:1 EDA/MELA, selectivity is worse than at the 3:1 mole ratio and supports the general conclusion reached in Example 12 of U.S. 4,036,881 that complex and noncyclics are predominant in the product.

Runs 5C-7C show that, with a 1:1 molar feed ratio of ethylenediamine:monoethanolamine, liquid phase operating conditions are encountered at 252° C. A high concentration of catalyst (35 ppm PO$_4$) is found in the effluent from reaction of a 1:1 mole ratio EDA:MELA feed even at 252° C. (Run 5-C). Although moderate conversion to predominantly noncyclic polyamines is initially obtained, continued operation under these conditions leads to poor conversion and selectivity, owing to catalyst losses in the product (see also Runs 6-C, 7-C). In contrast, the process of this invention, operation in the vapor phase with a molar excess of EDA, permits production of polyamines at temperatures as low as 240° C. with moderate conversion, production of predominantly noncyclic polyamines, and no catalyst degradation over time (Runs 5, 6, and 11).

What is claimed is:

1. In a fixed bed catalytic process for preparing polyethylene polyamines by reacting ethylenediamine with monoethanolamine in the absence of ammonia or inert gas in the presence of a solid phase phosphorous containing catalyst under vapor phase conditions, the improvement for enhancing selectivity to linear polyethylenes polyamines while maintaining high conversion which comprises maintaining said vapor phase conditions within a temperature range from about 200° to 280° C., a mole ratio of ethylenediamine to monoethanolamine, of from 2 to 12:1 and a pressure of from 30 to about 75 psig.

2. The process of claim 1 wherein the catalyst comprises a phosphorus containing compound compounded into a particulate material or carried upon a support.

3. The process of claim 2 wherein the phosphorus containing compound is selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorus acids, rare earth metal hydrogen phosphates, and phosphoramides.

4. The process of claim 5 wherein said catalyst comprises phosphoric acid on silica.

5. The process of claim 1 wherein said phosphate containing catalyst is phosphoric acid.

6. The process of claim 1 wherein said catalyst is ammonium hydrogen phosphate on silica.

7. The process of claim 1 wherein the mole ratio of ethylenediamine to monoethanolamine is from 3 to 9:1.

8. The process of claim 7 wherein the temperature is from about 245° to 276° C.

* * * * *